(12) United States Patent
Frot et al.

(10) Patent No.: US 8,654,330 B2
(45) Date of Patent: Feb. 18, 2014

(54) PARTICLE SIZE ANALYZER

(75) Inventors: Didier Frot, Saint Germain en Laye (FR); David Jacob, Canejan (FR)

(73) Assignees: IFP Energies Nouvelles, Rueil-Malmaison (FR); Cordouan Technologies, Pessac (FR)

( * ) Notice: Subject to any disclaimer, the term of this patent is extended or adjusted under 35 U.S.C. 154(b) by 0 days.

(21) Appl. No.: 13/379,715

(22) PCT Filed: Jun. 24, 2010

(86) PCT No.: PCT/FR2010/000470
§ 371 (c)(1),
(2), (4) Date: May 30, 2012

(87) PCT Pub. No.: WO2010/149885
PCT Pub. Date: Dec. 29, 2010

(65) Prior Publication Data
US 2012/0250019 A1    Oct. 4, 2012

(30) Foreign Application Priority Data
Jun. 26, 2009    (FR) .................................... 09 03167

(51) Int. Cl.
*G01N 21/00* (2006.01)
*G01N 21/53* (2006.01)

(52) U.S. Cl.
CPC ....................................... *G01N 21/53* (2013.01)
USPC ............................................. 356/342; 356/337

(58) Field of Classification Search
CPC ............................... G01N 21/00; G01N 21/53
USPC .................................................. 356/332–342
See application file for complete search history.

(56) References Cited

U.S. PATENT DOCUMENTS

| | | | |
|---|---|---|---|
| 4,402,614 A | 9/1983 | Porath-Furedi | |
| 5,572,321 A * | 11/1996 | Pinier et al. | 356/338 |
| 6,614,532 B1 | 9/2003 | Power et al. | |
| 6,628,397 B1 | 9/2003 | Nikoonahad et al. | |
| 2002/0034762 A1 | 3/2002 | Muller et al. | |

FOREIGN PATENT DOCUMENTS

| | | |
|---|---|---|
| EP | 0 654 661 A1 | 5/1995 |
| JP | 8-178825 A | 7/1996 |
| JP | 9-236534 A | 9/1997 |
| JP | 10-325791 A | 12/1998 |

* cited by examiner

*Primary Examiner* — Michael P Stafira
(74) *Attorney, Agent, or Firm* — Antonelli, Terry, Stout & Kraus, LLP.

(57) ABSTRACT

The present invention is a device for measuring the intensity of the light scattered by a thin film of a colloidal medium, comprising a monochromatic light source, a convergent optical system focusing the source onto the thin film to be analyzed comprising a dioptric element with one of the faces thereof constituting a first wall defining the thin film, at least one photosensitive detector producing a signal representing light scattered or backscattered by the thin film and means for processing the signal. A second wall of the device has a plane surface at the end of a rod.

7 Claims, 6 Drawing Sheets

PARTICLE SIZE ANALYZER

BACKGROUND OF THE INVENTION

1. Field of the Invention

The present invention relates to an improved device for measuring the intensity of the light scattered by high concentrations of particles or macromolecules of a size ranging between a few nanometers and several hundred nanometers. It more particularly applies to the correlation of photons in liquid media.

2. Description of the Prior Art

Document EP-0,654,661 A1 describes light scattering measurements performed on a thin film by a first dioptric interface and a measuring finger. FIG. 1 is a cross-sectional view of the device according to this prior document. It comprises a prism P, of angle A=90°, for totally reflecting a laser beam L. The faces of the prism form a diopter, which is an optical surface separating two media of different refractive indices. The laser beam enters through face E which is totally reflected by secant face F which exits through the normal of face S. Face S is topped by a part N with a channel therethrough defining a tank for receiving a volume of a sample containing objects M to be analyzed. The device also comprises a micropositioner G holding a bar H carrying at one end thereof a black glass rod D for limiting the reflected or scattered light intensity to prevent a parasitic intensity from reaching photodetector I. Advantageously, rod D has a (convex) radius of curvature for selectively providing a film as thin as possible for creating an analysis zone of the order of 1 mm$^2$.

However, this device has drawbacks:

Rod and/or prism surface damage occurs after several uses which is likely to lead to artifacts due to the intensity of light which is scattered by these micro-scratches that appear over time.

The convex finger is delicate to manufacture in view of the polishing operation (Lambda/4 tolerance) being difficult for curved shapes which significantly increases the cost of this part, The black rod can cause residual reflectivities that interfere in the measurement.

It is impossible to perform a measurement under flow without the latter disturbing the measurement due to the small surface of contact of the rod.

SUMMARY OF THE INVENTION

The present invention relates to a device for measuring the intensity of the light scattered by a thin film of a colloidal medium, comprising:

a monochromatic light source;

a convergent optical system for focusing the source onto the thin film to be analyzed comprising a dioptric element with one of the faces thereof constituting a first wall defining the thin film;

at least one photosensitive detector providing a signal representing the light scattered or backscattered by the thin film; and means for processing the signal provided by the photodetector.

The present invention improves the prior device by providing notably a new finger and rod geometry allowing, among other things, performing a measurement under flow of a liquid in the cell, to facilitate manufacture of the rod, to provide a simplified measurement implementation mode and not to damage the diopter by scratching the surface thereof.

Measuring the intensity of the light scattered by thin films, notably of colloidal media, is an objective of the present invention.

According to the device of the invention, a second wall comprising a plane surface is at the end of a rod. The device of the invention comprises means for positioning the plane surface at a predetermined distance from the first wall and means for maintaining a substantially parallel orientation (parallelism) between the two walls.

The rod can be made of a transparent material mounted in a body.

The face of the other end of the rod forms an angle $\alpha$ with the plane surface and is in contact with a liquid of predetermined refractive index to limit reflection and scattering disturbances.

The end of the body can comprise sealing means for isolating the thin film present below the rod.

The finger can be rotated about an axis thereof by a means providing rotation and can carry cleaning means over a portion of the plane surface.

The body can comprise an optical lens and a CCD detector.

The end of the rod can comprise electrodes providing Zeta potential measurements on the thin film.

The rod mounted in a body can be within a housing including the dioptric element. The housing includes an inlet orifice and an outlet orifice for the colloidal medium which provides for circulation of the medium in the housing.

The light source can be transmitted to the optical system by an optical fiber, and the scattered light can be transmitted to a measuring means by an optical fiber.

The plane surface can have a surface area of at least 10 mm$^2$.

BRIEF DESCRIPTION OF THE DRAWINGS

Other features and advantages of the present invention will be clear from reading the description hereafter of embodiments given by way of non limitative example, with reference to the accompanying figures wherein.

DETAILED DESCRIPTION OF THE INVENTION

The present invention is based on a finger capable of forming a thin film between two plane surfaces having a high level of relative parallelism. The thin film of colloidal media allows measuring the scattered intensity.

Figure 1:
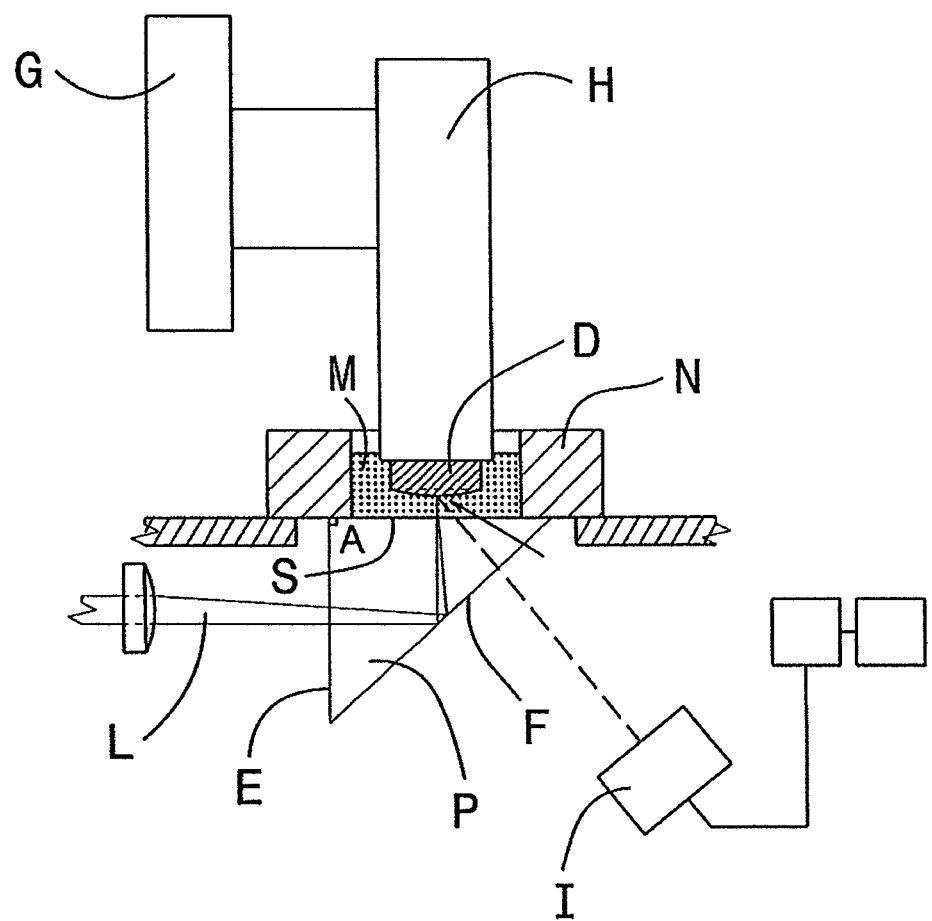
FIG. 1 diagrammatically shows a device according to the prior art.
Figure 2A:
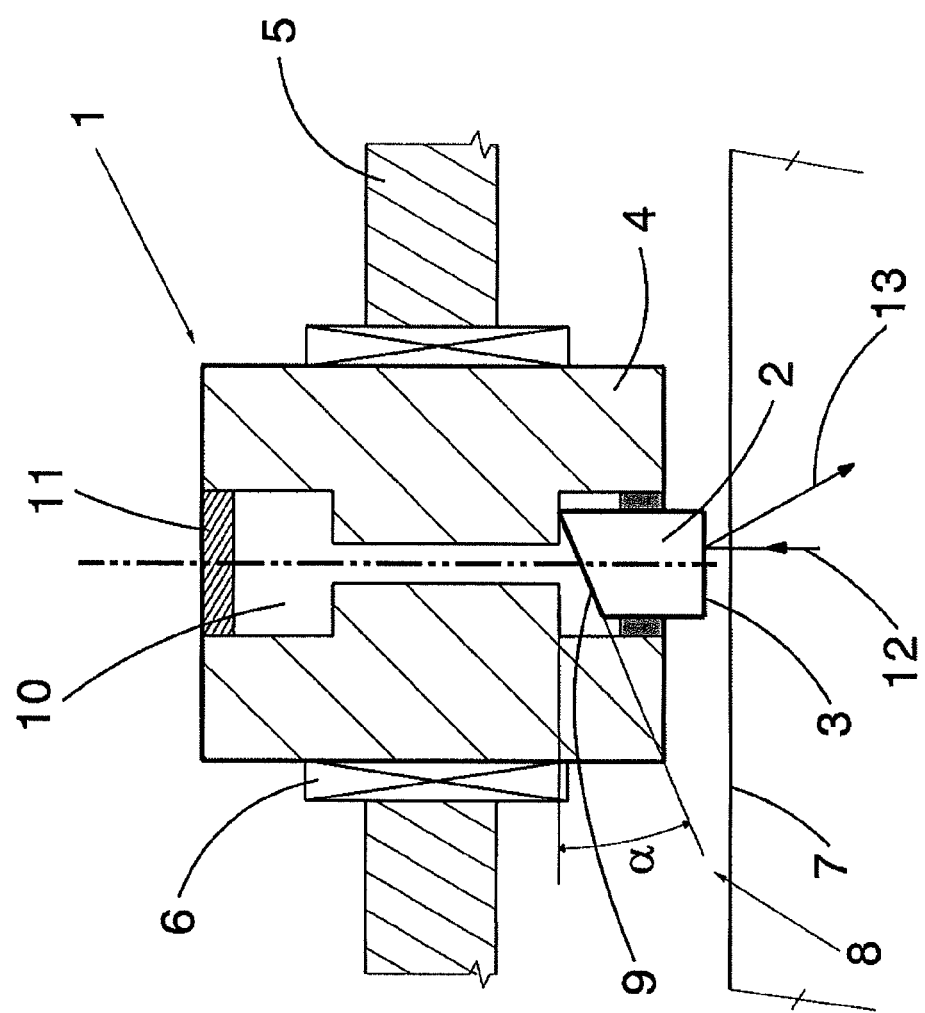
FIG. 2a diagrammatically illustrates, in cross-sectional view, an embodiment of a finger of the device according to the invention.
Figure 2:
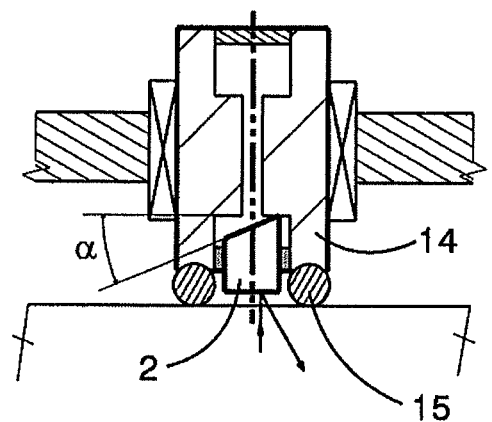
FIG. 2b illustrates another embodiment of the finger as assembled.

FIG. 2a diagrammatically shows the device according to the invention. Finger 1 is a glass rod 2, or equivalent, which defines at the end thereof a plane surface 3. The rod is held in a body 4. The optical specifications of the faces of the cylindrical rod are standard specifications, that is a Lambda/4 surface state and a Lambda/2 planeity.

Body 4 is mechanically linked to an upper part, or cover, of a housing 5 by fastening and positioning means 6 whose purpose is to provide sealing between the body and the housing, to provide means for adjusting the thickness of the thin film, that is the distance between lower face 3 of rod 2 and diopter and to provide parallelism between face 3 of the rod and the diopter 7.

The parallelism between the lower face of the finger and the upper face of the prism (diopter) making up the bottom of tank 8 is provided by self-adjustment by means of a mechanical play, by the adjustment of the fastening means 6. This play can be achieved by means of a short guide length (twice the diameter of the finger for example) of the body of the finger in the housing cover. This self-adjustment can also be obtained by adjusting the machining tolerances of the sleeve guide bore.

Surprisingly enough, it has been observed that it is the drainage of the liquid film under the action of the thrust exerted on the finger that provides perfect parallelism of lower face 3 of the finger with upper face 7 of the tank, insofar as the rod, or the body holding the rod, has a sufficient degree of freedom for self-adjustment. Thus, the rod may be considered to sit on a liquid cushion.

Fastening means 6 can also advantageously comprise an axial play allowing, for example under the action of tapping, for example by an operator's finger, to remove fluid film (flushing). This movement, which decreases or even cancels out the film thickness, can be against the action of a return spring.

Upper face 9 of the rod is preferably inclined by an angle α (about 5 degrees) to the lower face so as not to disturb the backscattered light. Furthermore, the inner volume 10 of body 4 contains a refraction medium suited to minimize this disturbance. The volume is closed by a plug 11.

Incident laser beam 12 is transported to the measuring point by known optical means, notably those described in document EP-0,654,661 A1 mentioned here by way of reference. The same applies to the measuring means for scattered ray 13.

The device according to the invention thus affords the following advantages:

When the finger is positioned in contact with the prism, a liquid film confined between the two plane faces (the diopter(s) and rod) is motionless and insensitive to the environment of the rod, and notably to flows.

The finger can be rapidly moved near to the diopter without worrying about the impact effect on the surface because the thin film provides a buffer that mutually protects each surface against shocks and scratches.

This configuration is used for a flushing function that allows renewal of the thin film of the sample and optimization of the homogeneity in temperature, concentration and statistical distribution of the constituents of the sample in case of a mixture.

Removal, in the thin film which is analyzed, of possible aggregates or unwanted dusts.

A shear effect is obtained in the thin film, which can separate weakly bonded aggregates.

The parallelism of the lower face of the finger with the upper face of the tank allows obtaining concentric interference rings (no air wedge effects) and therefore to precisely monitor by optical interferometry the film drainage stage. This is a pertinent indicator of the stationary state of the liquid film to be analyzed.

FIG. 2b illustrates another embodiment of the finger of the device according to the invention where body 14 comprises end sealing means 15 which insulates a medium portion around the thin film trapped below the rod. This embodiment is particularly suited for highly diluted and therefore weakly scattering media.

Figure 3:
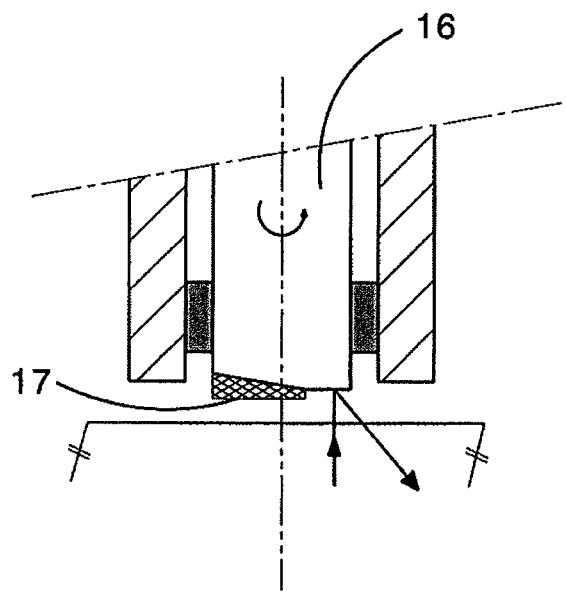
FIGS. 3a and 3b show another embodiment of the end of the rod.
Figure 3:
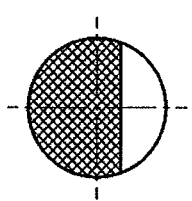

FIGS. 3a and 3b illustrate another embodiment of a rod 16 held in a body 4. The cylindrical rod carries, over at least half the surface of the face, a cleaning set 17. The other part of the surface remains available as the measuring point. The rod can be rotated about its longitudinal axis to clean the total surface of the face of the rod, notably the measuring point, by partly flexible microsticks made from a material compatible with a large number of acidic or basic organic solvents. Industrial media are often concentrated and they sometimes include aggregates when the dispersion is not homogeneous. In order to overcome analysis difficulties with such systems, this option can be used instead of filtering the solutions. FIG. 3b shows a bottom view of the face of the rod.

Figure 4:
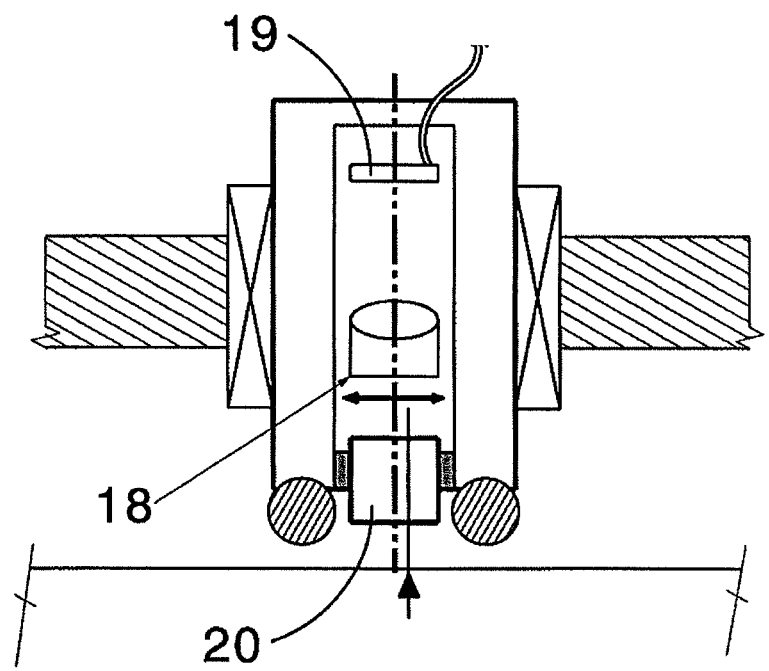
FIG. 4 diagrammatically shows another embodiment of the finger carrying the rod.

FIG. 4 shows an embodiment of the finger combined with a set of optical constituents 18 equivalent to a microscope lens to which a CCD camera 19 is added. Rod 20 can be thin, with parallel faces. In this case, it acts as a protective porthole for microscope lens 18, which prevents having to use an immersion lens, which is very costly. Focusing the image of the thin film on the CCD detector is provided by an extension tube (of variable extension) or a system of optical lenses with variable focal lengths that can, for example, be controlled electrically for example.

Figure 5:
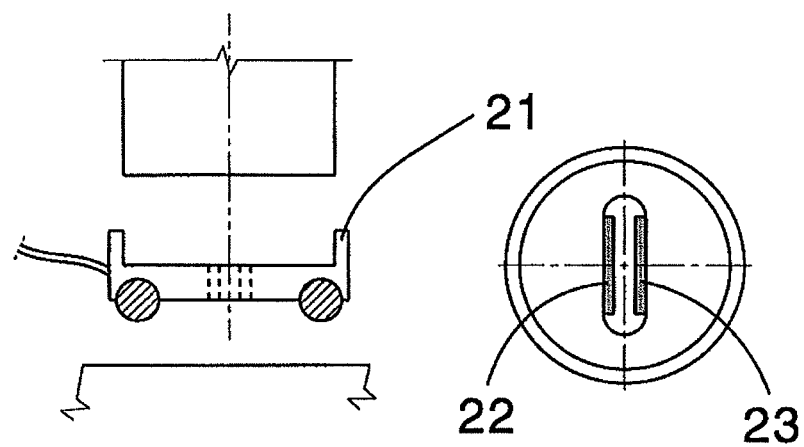
FIG. 5 shows another device for performing another type of measurement.

FIG. 5 illustrates a possibility measurement complementary to photon counting. It provides access to a measurement of the Zeta potential for a wide particle distribution through the combination of the scattered intensity analysis (small particle range generally below one micron) and of the electrophoretic mobility analysis by an image processing (see above), or the wavelength shift of the intensity scattered by particles under forced movement (one-directional displacement).

One of the embodiments is a cylindrical rod 21 bored over about one millimeter and comprising two metallic electrodes 22 and 23 on the walls of the bored zone, and arranged parallel to one another. In the volume defined by the bore when the finger is in contact, the Zeta potential can be measured.

Figure 6:
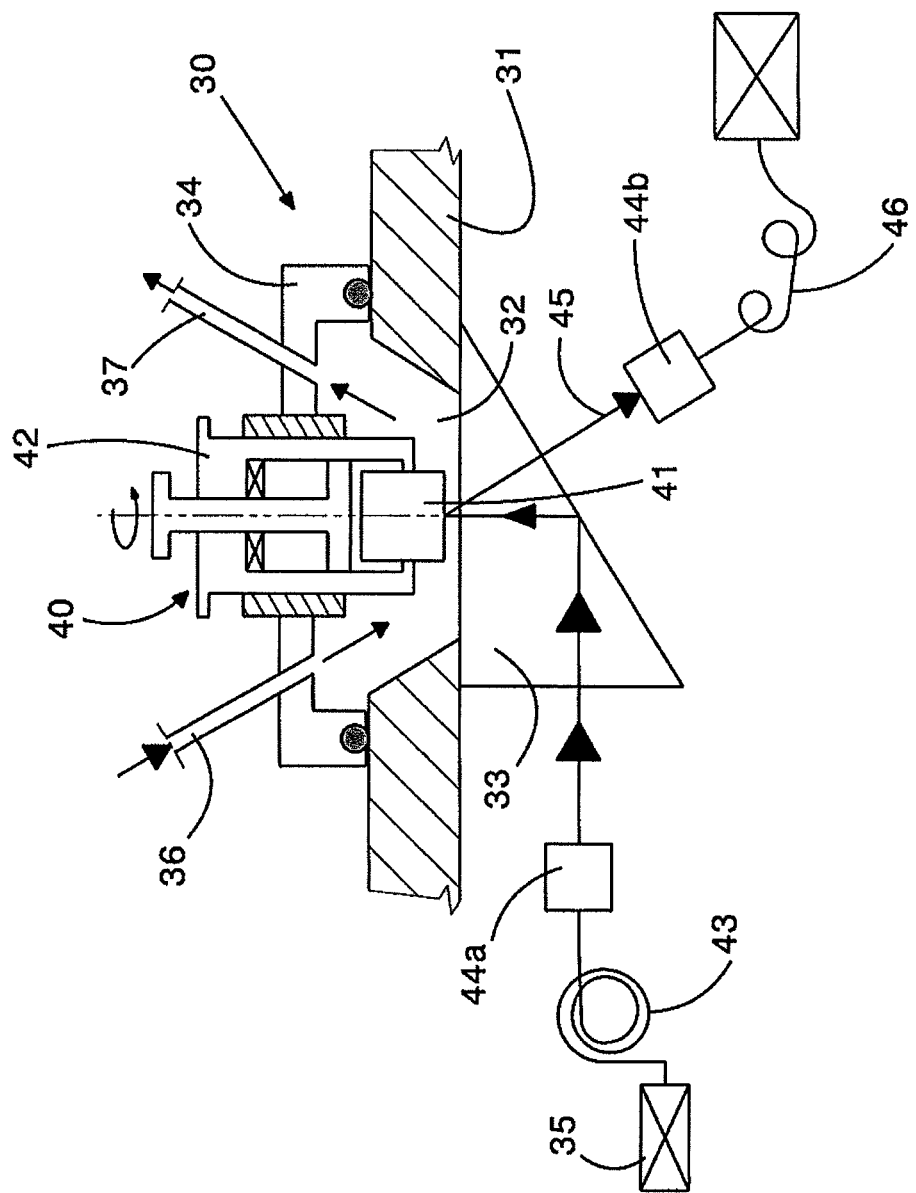
FIG. 6 illustrates the device according to the invention for making measurements during medium circulation.

FIG. 6 shows a system integrating the device according to the invention for in-line measurements. Device 30 comprises a support 31 through which a cavity 32 extends which is closed by a prism 33 and a housing 34. Housing 34 is in hydraulic communication through lines 36 and 37. The entire measuring finger 40 is made up of a rod 41 and a body 42 according to the present description. Laser beam 35 can be transmitted to prism 33 by an optical fiber 43 and a collimator 44a. The scattered intensity signal 45 collected by a collimator 44b can be transmitted to a measuring means and to a PC through an optical fiber 46. In general, optical signals can be transmitted by optical fibers, whether in the in-line measurement version according to FIG. 6 or otherwise.

The system according to FIG. 6 provides a measuring method based on the functionalities of the finger device capable of defining a thin film between two walls. This finger has two positions with one spaced from the prism, the other in contact with the prism for measurement.

When the finger is at a distance from the wall, the fluid circulates in cavity 32 and it is renewed according to the circulation of the medium in lines 35 and 36. When contact with the prism is imposed on the finger by maintaining a predetermined pressure thereon, it immobilizes and isolates at least part of a liquid film trapped between the two interfaces which allows the stream to bypass the finger without disturbing the measurement. This is possible from the sufficiently wide plane surface of the rod that enables the measuring point to be isolated from its environment. The diameter of the rod is for example at least greater than 5 mm which guarantees sufficient isolation of at least a portion of the liquid film, combined with the self-adjustment of the parallelism of the faces at the measuring point. It can be noted that, in this measurement range under scattered intensity flow, the parallelism of the faces is an essential condition for the measurement.

It is also possible, according to the embodiment described in FIG. 2b, to immobilize the liquid film by integrating a joint at the end of the body. The joint is selected sufficiently supple so that, once compressed, the surface of the finger is in contact with the lower diopter while isolating a film.

It is also possible, according to the embodiment described in FIG. 4, to equip the finger with a microscope lens and a camera. Measuring on a liquid film at rest does not require a high-speed camera for imaging the particles. Under such conditions, using a camera with a high spatial resolution (large number of small pixels) has the advantage of allowing measurement of particles of smaller size.

Using the measuring device according to the invention thus affords many advantages:

It is not necessary to take a sample, which eliminates the doubt about the sample being representative and simplifies the operating mode of the measurement. In fact, the liquid medium can be carried from a process directly into measuring cavity 32 through lines 36 or 37. The measurement can be repeated as often as needed with the finger being moved away and then finger being moved in contact without pressure drop in the line, The measurement is a conventional dynamic light scattering measurement that requires no additional hypotheses regarding the movement of the particles.

Figure 7:
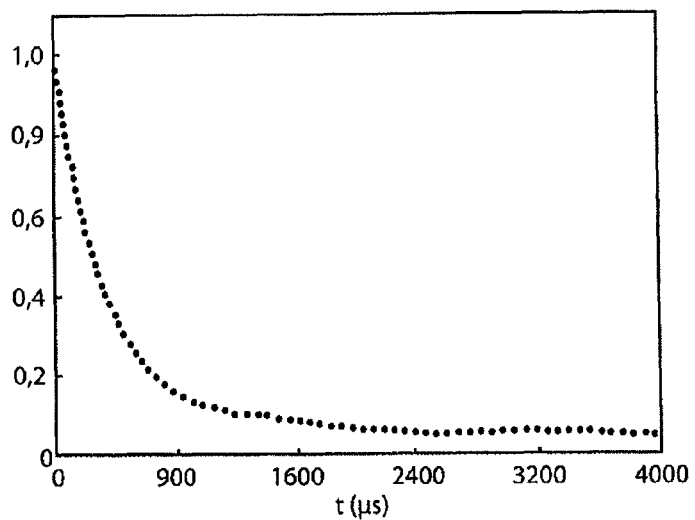
FIGS. 7, 8 and 9 show measurement results obtained respectively for a sampling of standard media without flow, with flow and the finger raised and with flow and the finger in contact position.
Figure 8:
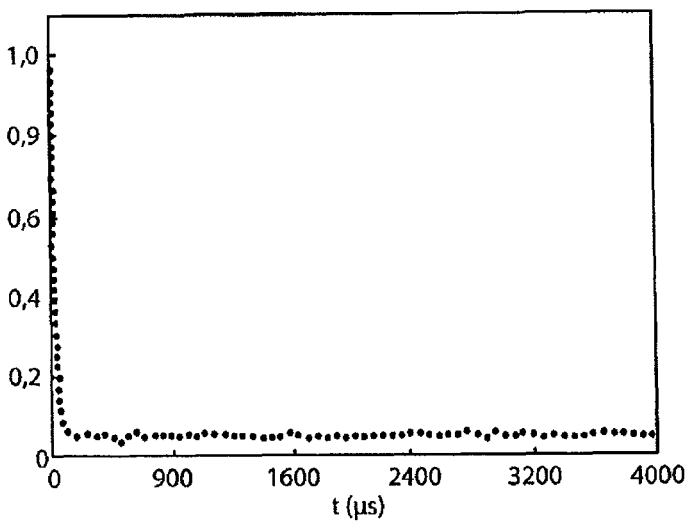
Figure 9:
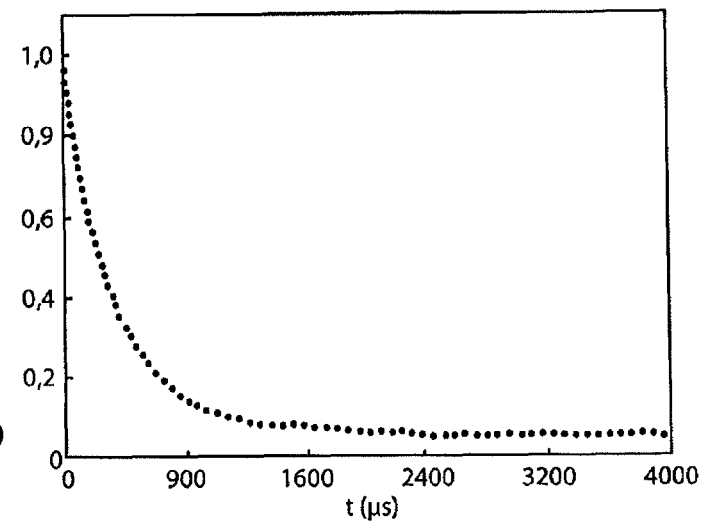

FIGS. 7, 8 and 9 show the efficiency of the measuring device and method.

These graphs show the autocorrelation function of the scattered intensity over time on the abscissa and the amplitude on the ordinate. It is from these curves that the size of the objects responsible for the scattered intensity is extracted. FIG. 7 shows the autocorrelation curve of a reference standard, which is a monomodal latex standard with a hydrodynamic diameter of 160 nanometers. It is known that there is a proportionality relation between the size of the objects and the slope at the origin of the autocorrelation curve.

FIG. 8 gives the autocorrelation curve of the same standard in the presence of a flow (with a system of the type shown in FIG. 6) with the finger at a distance from the surface of the prism. It can be observed that a flow modifies the slope at the origin since the latter is approximately here 30 times smaller than the one obtained by measuring the standard (FIG. 7). This consequently decreases the apparent size by the same factor, producing as a result pseudo-objects with a diameter of 6 nanometers instead of 160 nm.

FIG. 9 gives the autocorrelation curve of the same standard in the presence of a flow, but with the finger in contact with the surface. The measurement performed here with the finger in contact gives a size measurement result in agreement with the measurement obtained for the standard in the absence of flow, which shows that at least part of the film trapped below the rod is motionless.

The invention claimed is:

1. A device for measuring intensity of scattered or backscattered light by a film of a colloidal medium, comprising:
   a monochromatic light source;
   a convergent optical system for focusing the light of the source onto the film to be analyzed and comprising a dioptric element with a face which is a first wall defining the film;
   at least one photosensitive detector for providing a signal representing the light scattered or backscattered by the film;
   means for processing the signal;
   a second wall comprising a plane surface at the end of a rod, the rod comprising a transparent material mounted in a body;
   means for positioning the plane surface at a predetermined distance from the first wall; and
   means for maintaining the first and the second walls to be substantially parallel; and wherein
   an end of the body comprises sealing means for isolating the film below the rod.

2. A device as claimed in claim 1 wherein:
   a face of another end of the rod forms an angle with the plane surface and is in contact with a liquid of predetermined refractive index to limit reflection and scattering disturbances.

3. A device for measuring intensity of scattered or backscattered light by a film of a colloidal medium, comprising:
   a monochromatic light source;
   a convergent optical system for focusing the light of the source onto the film to be analyzed and comprising a dioptric element with a face which is a first wall defining the film;
   at least one photosensitive detector for providing a signal representing the light scattered or backscattered by the film;
   means for processing the signal;
   a second wall comprising a plane surface at the end of a rod, the rod comprising a transparent material mounted in a body;
   means for positioning the plane surface at a predetermined distance from the first wall; and
   means for maintaining the first and the second walls to be substantially parallel;
   an end of the body comprises sealing means for isolating the film below the rod; and wherein:
   the rod comprises means for rotating the rod about an axis thereof and the rod carries means for cleaning a portion of the plane surface.

4. A device as claimed in claim 1 wherein:
   the body comprises an optical lens and a CCD detector.

5. A device for measuring intensity of scattered or backscattered light by a film of a colloidal medium, comprising:
   a monochromatic light source;
   a convergent optical system for focusing the light of the source onto the film to be analyzed and comprising a dioptric element with a face which is a first wall defining the film;
   at least one photosensitive detector for providing a signal representing the light scattered or backscattered by the film;
   means for processing the signal;
   a second wall comprising a plane surface at the end of a rod;
   means for positioning the Diane surface at a predetermined distance from the first wall; and
   means for maintaining the first and the second walls to be substantially parallel; and wherein an end of the rod comprises electrodes for making Zeta potential measurements of the film.

6. A device for measuring intensity of scattered or backscattered light by a film of a colloidal medium, comprising:
- a monochromatic light source;
- a convergent optical system for focusing the light of the source onto the film to be analyzed and comprising a dioptric element with a face which is a first wall defining the film;
- at least one photosensitive detector for providing a signal representing the light scattered or backscattered by the film;
- means for processing the signal;
- a second wall comprising a plane surface at the end of a rod;
- means for positioning the plane surface at a predetermined distance from the first wall; and
- means for maintaining the first and the second walls to be substantially parallel; and wherein
- the rod mounted in the body includes a housing containing a dioptric element and an inlet orifice and an outlet orifice for providing circulation of the colloidal medium in the housing.

7. A device as claimed in claim 1, wherein the plane surface has a surface area of at least 10 mm$^2$.

* * * * *